(12) United States Patent
Kohler et al.

(10) Patent No.: US 7,449,145 B2
(45) Date of Patent: *Nov. 11, 2008

(54) METHOD FOR DETERMINING LUMEN PENETRATION OF A VAPOR PHASE STERILANT

(75) Inventors: James P. Kohler, Laguna Hills, CA (US); Harold R. Williams, San Clemente, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/615,368

(22) Filed: Dec. 22, 2006

(65) Prior Publication Data

US 2007/0160491 A1    Jul. 12, 2007

Related U.S. Application Data

(63) Continuation of application No. 10/112,518, filed on Mar. 29, 2002, now Pat. No. 7,186,372.

(51) Int. Cl.
*A61L 2/20* (2006.01)
(52) U.S. Cl. ............................. 422/3; 422/28
(58) Field of Classification Search ...... 422/3, 422/28
See application file for complete search history.

(56) References Cited

U.S. PATENT DOCUMENTS

| 4,834,852 | A |  | 5/1989 | Wabner |
|---|---|---|---|---|
| 4,843,867 | A |  | 7/1989 | Cummings |
| 4,956,145 | A |  | 9/1990 | Cummings |
| 5,527,508 | A |  | 6/1996 | Childers |
| 5,788,925 | A |  | 8/1998 | Pai |
| 6,156,257 | A |  | 12/2000 | Tachi |
| 6,269,680 | B1 |  | 8/2001 | Prieve |
| 6,582,708 | B1 |  | 6/2003 | Sagel |
| 7,186,372 | B2 | * | 3/2007 | Kohler et al. .................. 422/3 |
| 2001/0036670 | A1 |  | 11/2001 | Fryer |
| 2003/0012689 | A1 |  | 1/2003 | Caputo |

FOREIGN PATENT DOCUMENTS

EP          1166802 A       1/2002

OTHER PUBLICATIONS

J.C. Slattery and R.B. Bird, "Aiche Journal", 4, 137-142, 1958. Claculation of the Diffusion Coefficient of Dilute Gases and of the Self-Diffusion Coefficient of Dense Gases.
Schumb et al., Reinhold Pub. Co., NY, 1955, p. 226., "Hydrogen Peroxide".

* cited by examiner

*Primary Examiner*—Elizabeth L McKane

(57) ABSTRACT

Concentration of a chemical vapor sterilant, especially, hydrogen peroxide, can be calculated at a point within a lumen based upon physical characteristics of the lumen and process parameters of a sterilization process employing the sterilant.

18 Claims, 1 Drawing Sheet

METHOD FOR DETERMINING LUMEN PENETRATION OF A VAPOR PHASE STERILANT

RELATED APPLICATIONS

This application is a continuation of U.S. application Ser. No. 10/112,518 filed Mar. 29, 2002, now U.S. Pat. No. 7,186,372, the entire contents of which are hereby incorporated by reference.

BACKGROUND

The present invention relates to vapor phase sterilization, and more particularly to determining the penetration of vapor phase chemical sterilants into a lumen.

Presently, vapor phase chemical sterilization is a popular option for medical devices which are temperature sensitive. Vapor phase sterilization encompasses such sterilants as hydrogen peroxide, peracetic acid, ethylene oxide and chlorine dioxide. The chemical vapor diffuses into contact with and sterilizes the surface of the instrument. Penetration of long narrow lumens with the vapor represents one of the largest challenges. Determination of whether such penetration has been successful is a further challenge. Presently, it remains difficult to place a reliable sensor in a long narrow lumen. Such sensors are typically too large to be accommodated within the lumen and their presence may disturb the diffusion into the lumen.

Although, directly measuring concentration of a vapor sterilant inside the lumen remains a challenge, several methods have been put forward for directly measuring such concentration within a sterilization chamber of such a sterilization system. For instance, hydrogen peroxide concentration can be measured by passing lightwaves of certain frequencies through the chamber and detecting the absorption of the lightwaves to determine the makeup of the gases within the chamber. In another method, a thermocouple coated with a catalyst for breaking down hydrogen peroxide can be placed within the chamber and the degree of heating caused on the thermocouple by the breakdown of hydrogen peroxide can be used to indicate the concentration of hydrogen peroxide within the chamber. Of course, other methods may also be employed to measure the concentration of hydrogen peroxide or other chemical vapors within a sterilization chamber. However, such measurements do not reveal the concentration within a lumen of a device within a chamber.

The present invention overcomes this and other limitations in the prior art and provides a method for determining the concentration of a chemical vapor sterilant within a lumen of a device within a sterilization chamber.

SUMMARY OF THE INVENTION

A method according to the present invention assesses a sterilization of a lumen of a device in a vapor phase hydrogen peroxide sterilization process. The method comprises the steps of: a) measuring concentration of hydrogen peroxide vapor exterior of the lumen; b) calculating at least once a concentration of hydrogen peroxide at a selected location within the lumen based upon time of exposure, concentration of hydrogen peroxide exterior of the lumen and the physical characteristics of the lumen; and c) indicating a parameter relevant to said sterilization of said lumen based upon said concentration of said hydrogen peroxide at the selected location.

The step of indicating can comprise displaying to a user the parameter relevant to the sterilization of the lumen. Such parameter can comprise concentration of said hydrogen peroxide at the selected location. Steps a) and b) can be repeated multiple times to calculate an integrated value of the concentration of hydrogen peroxide at the selected location over a time of exposure and the parameter relevant to the sterilization of the lumen could comprises such integrated value. The parameter relevant to the sterilization of the lumen could be a success or failure of the sterilization of the lumen.

The process parameters used in the calculating step preferably comprise: pressure exterior of the lumen, the concentration of peroxide exterior of the lumen and time. The physical characteristics of the lumen used in the calculating step preferably comprise: diameter of the lumen, length of the lumen to the selected location, type of material forming the lumen and temperature of the material forming the lumen.

Preferably, the calculating step employs a mathematical model in which the lumen is assumed to have a single dimension. The calculating step can employs a mathematical model solved by iteration.

Preferably the concentration of hydrogen peroxide at the selected location is calculated based upon the following relationship:

$$c_p = c_o + (4k\, c_o/\pi)\{\Sigma[(\sin(n\pi x/L))((\exp(t(k - D(n\pi/L)^2))) - 1)/(n(k - D(n\pi/L)^2))]\} - (4c_o \exp(kt))\{\Sigma[(\sin(n\pi x/L))(\exp(-Dt(n\pi/L)^2))]\}/\pi;$$

where:
- $c_p$ represents the concentration of hydrogen peroxide at the selected location;
- $c_o$ represents the concentration exterior of the lumen;
- k represents a rate constant for losses of hydrogen peroxide;
- L represents the length of the lumen;
- D represents the diffusion coefficient for hydrogen peroxide vapor;
- x represents the distance into the lumen to the selected location from exterior of the lumen
- n represents odd integer counters 1, 3, 5, . . . ; and
- t represents the time from when hydrogen peroxide vapor first is introduced exterior of the lumen.

Preferably, k is determined at least in part based upon a material forming the lumen, the diameter of the lumen and the temperature of the material forming the lumen.

In one aspect of the invention, a method is provided for controlling sterilization of a lumen of a device in a vapor phase hydrogen peroxide sterilization process, the method comprising the steps of: measuring a concentration of hydrogen peroxide vapor exterior of the lumen; calculating at least once a concentration of hydrogen peroxide at a selected location within the lumen based upon process parameters of the sterilization process and physical characteristics of the lumen, wherein the process parameters include the concentration of hydrogen peroxide exterior of the lumen; and adjusting a parameter of the sterilization process based upon the at least one calculated concentration of hydrogen peroxide at the selected location.

The step of adjusting a parameter of the sterilization process can comprise adjusting a time of exposure of the device to the vapor phase hydrogen peroxide and/or adjusting the concentration of the hydrogen peroxide exterior of the lumen. The method can comprise repeatedly measuring the concentration of hydrogen peroxide exterior of the lumen and calculating the concentration of hydrogen peroxide at the selected location and modifying a parameter of the sterilization process upon achieving a preselected value of hydrogen peroxide at the selected location, such as for instance achieving a preselected value of the integrated time and concentration exposure at the selected location.

DETAILED DESCRIPTION

Figure 1:
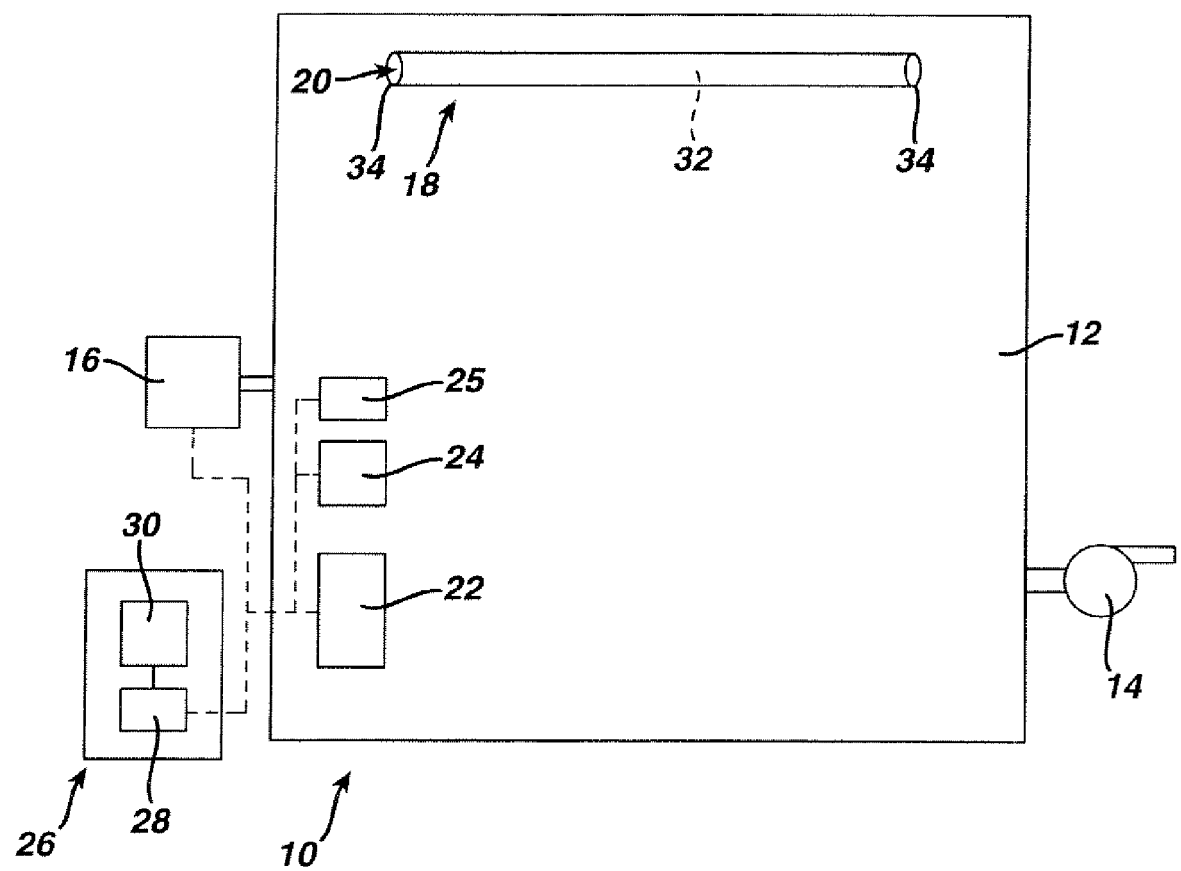
FIG. 1 is a block diagram of a sterilization system upon which the method of the present invention can be practiced.

FIG. 1 represents, in block diagram form, a sterilizer 10 comprising a chamber 12, a vacuum pump 14 for drawing a vacuum upon the chamber 12 and an injector 16 for injecting a sterilant, namely hydrogen peroxide, into the chamber 12. A medical device 18 having a lumen 20 is disposed within the chamber 12 for sterilization. A hydrogen peroxide sensor 22, temperature sensor 24 and pressure sensor read hydrogen peroxide concentration, and the temperature and pressure within the chamber 12 and provide their output to a control system 26 comprising a CPU 28 and display 30.

In its basic form, the sterilizer 10 operates by drawing a vacuum upon the chamber 12 via the pump 14 and injecting hydrogen peroxide into the chamber 12 with the injector 16. The hydrogen peroxide may enter the chamber in either vapor or liquid form, with any liquid hydrogen peroxide vaporizing upon entry into the low pressure environment of the chamber 12. Contact with the hydrogen peroxide vapor sterilizes the device 18.

To sterilize the lumen 20 hydrogen peroxide vapor must diffuse therein. The hydrogen peroxide sensor 22 can measure the concentration of hydrogen peroxide within the chamber 12 but cannot directly measure the concentration of hydrogen peroxide achieved within the lumen 20, especially at a difficult to penetrate midpoint 32 of the lumen 20. To overcome this limitation, the present invention provides a method for calculating the concentration of hydrogen peroxide achieved at a specific location, such as the midpoint 32, within the lumen 20 based upon parameters of the sterilization cycle and the physical parameters of the medical device 18.

The mathematical model of the present invention is based upon a mass balance for hydrogen peroxide at a point inside a mass transport-restricted region of the load, such as the center of a lumen 32. The mass balance around a lumen is in the form of a differential equation, an initial condition and a boundary condition:

$$\partial c_p / \partial t = D \nabla^2 c_p + k c_p$$

Initial condition: $t=0$, $c_p=0$ everywhere
Boundary condition: $c_p = c_o$ at the two ends of the lumen
$c_p$ = hydrogen peroxide concentration at the point of interest in the lumen, g/cm³
$t$ = time
$D$ = diffusion coefficient, cm²/sec
$\nabla^2$ = differential operator, $\partial^2 / \partial x^2$ for one-dimensional diffusion in the x-direction, cm⁻²
$k$ = rate constant for losses in the lumen, sec⁻¹
$c_o$ = hydrogen peroxide concentration at the two entrances to the lumen, g/cm³

The differential equation states that:

The change of peroxide mass per volume with time=The rate of mass input per volume by diffusion+The rate of mass input per volume by internal processes On the right side of the equation, the rate of delivery of hydrogen peroxide mass per volume is specified by the diffusion term, which is driven by the concentration gradient from the chamber 12 to the lumen 20. The rate of mass input per volume to the lumen 20 by internal processes is a negative term, whenever mass is lost in the lumen 20 by decomposition, absorption, adsorption and condensation. In that case the rate constant k is a negative number.

The initial condition requires that the concentration of hydrogen peroxide is zero in the sterilizer chamber 12 and lumen 20 before injection of hydrogen peroxide.

The boundary condition sets the hydrogen peroxide concentration equal to $c_o$ in the chamber 12 at both entrances 34 to the lumen. In practice this value changes with time during the sterilization cycle, but an analytical solution may be obtained for the one-dimensional case with constant external concentration and position-invariant diffusion coefficient to give a useful calculation of the lumen concentration with time. The analytical solution to this case is a complicated set of terms and variables, which must be evaluated to solve for the lumen concentration:

$$c_p = c_o + (4k\, c_o / \pi)\{\Sigma[(\sin(n\pi x/L))((\exp(t(k-D(n\pi/L)^2)))-1)/(n(k-D(n\pi/L)^2))]\} - (4c_o \exp(kt))\{\Sigma[(\sin(n\pi x/L))(\exp(-Dt(n\pi/L)^2))/n]\}/\pi$$

This solution assumes that the initial hydrogen peroxide concentration $c_i$ in the chamber 12 and load of devices 18 is $c_p=0$. A more general solution would be obtained by replacing $c_o$ with $(c_o-c_i)$ in the second and third terms of the solution equation above to allow for a non-zero initial hydrogen peroxide concentration.

The hydrogen peroxide concentration in the chamber 12 is measured at each time point after injection by the peroxide monitor 22. In the solution equation above, the concentration $c_o$ at both lumen entrances may be estimated as the hydrogen peroxide concentration in the chamber 12, because the resistance to mass transfer is generally small from the bulk region of the chamber 12 to the periphery of the load.

The summation of terms Σ in the solution occurs over the series n=1, 3, 5 . . . ∞.

The position of interest, x, in the lumen 20 may be anywhere along the axis from x=0 cm at one end 34 of the lumen 20 to x=L cm at the other end. At the center 32 of the lumen 20, which is usually the most mass-transport restricted region, x/L=0.5.

The solution is evaluated in one-second time points t after injection.

The diffusion coefficient D for hydrogen peroxide is calculated with the published correlation (Ref. J. C. Slattery and R. B. Bird, *AIChE Journal*, 4, 137-142, 1958)

$$D = 3.303 \times 10^{-4}((T+273)^{2.334})/P$$

Lumen temperature T° C. and chamber pressure P mmHg can be measured during the sterilization cycle to evaluate D. As the temperature of the material forming the lumen 20 changes only moderately in most sterilization cycles, it can be assumed to be the room temperature at which the device 18 was stored prior to the process.

The rate constant k cannot be measured experimentally inside the lumen 20 without disturbing the internal environment, so a value is assigned for each lumen material, such as stainless steel and polyethylene. The value is adjusted to provide an area scale, which correlates efficacy results from the sterilization cycles, as discussed below.

The concentration at the center 32 of the lumen 20 is calculated from the analytical solution equation at each time point during the injection and diffusion steps of the sterilization cycle with the variables as defined above. For cycles with a venting step after injection of hydrogen peroxide, the concentration in the lumen 20 during the first minute of diffusion is set equal to the chamber concentration, because hydrogen peroxide is driven by air pressure into the lumen 20. Concentration in the lumen 20 for the remainder of the diffusion step is calculated by subtracting losses of decomposition, absorption, adsorption and condensation.

Efficacy of the sterilization cycle depends strongly upon the concentration of hydrogen peroxide in the chamber 12 and in the load. However, other process variables are also important, such as chamber and load temperature, size and composition of the load and exposure time. For a fixed load configuration in a particular sterilizer with a qualified sterilization cycle, temperature remains relatively constant during injection, so concentration and exposure time become the most important control variables. Area under a concentration-time curve is a useful index for quantifying cycle performance to compare with efficacy as measured via biological indicators.

An estimate of the area under the concentration-time curve is obtained by summing the one-second concentration values in the injection and diffusion steps of the cycle, as shown in Table 1 for sterilization cycles in a STERRAD® 200 hydrogen gas/plasma sterilizer available from Advanced Sterilization Products division of Ethicon, Inc., Irvine, Calif., with different lumens in the validation load. The area scale for stainless steel (SS) is established by setting the value of the rate constant k equal to 0.46 sec$^{-1}$ to give an area of approximately 100 mg–sec/l for the cycles with 3 mm×500 mm stainless steel lumens at 30° C. This set of lumens is chosen as the basis for the stainless steel area scale, because 3 mm×500 mm stainless steel lumens are at the limit of the presently approved label claims for the STERRAD® 200 Sterilizer, so they represent one measure of a borderline capability for efficacy.

TABLE 1

Results for the STERRAD ® 200 Sterilizer
Model for Hydrogen Peroxide Concentration in Lumens
Diffusion, Venting and Reaction Processes

| Lumen, mm dia. × mm long | Temp., ° C. (lumen material) | Injection Time, min. | -k, sec$^{-1}$ | Mid-Lumen Hydrogen Peroxide Conc. vs. Time Area, mg-sec/l | Fraction Positive Biological Indicators |
|---|---|---|---|---|---|
| 3 × 400 SS | 30 | 6.5 | 0.46 | 168, 156, 157 | 0/72 |
| 3 × 500 SS | 30 | 6.5 | 0.46 [a] | 101, 93, 91 | 0/96 |
| 3 × 400 SS | 30 | 2 | 0.46 | 106, 104, 108 | 0/72 |
| 3 × 400 SS | 30 | 1 | 0.46 | 97, 100, 108 | 4/72 |
| 3 × 400 SS | 5 | 6.5 | 1.41 [c] | 53, 50, 50 | 1/72 |
| 1 × 125 SS | 30 | 6.5 | 4.14 [d] | 139, 143, 149 | 0/36 |
| 0.8 × 100 SS | 30 | 6.5 | 6.47 [e] | 133, 137, 140, 136 | 0/48 |
| 0.8 × 150 SS | 30 | 6.5 | 6.47 | 43, 44 | 2/24 |
| 1 × 500 PE | 30 | 6.5 | 0.33 [a] | 104, 107, 108 | 0/36 |
| 1 × 700 PE | 30 | 6.5 | 0.33 | 34 | 1/12 |
| 3 × 1000 PE | 30 | 6.5 | 0.037 [f] | 262, 261, 245 | 0/36 |
| 3 × 1500 PE | 30 | 6.5 | 0.037 | 99, 102, 97 | 1/36 |
| 3 × 1500 PE | 30 | 20 | 0.037 | 179 | 0/12 |
| 3 × 1500 PE | 30 | 25 | 0.037 | 188 | 0/12 |
| 3 × 1500 PE | 30 | 30 | 0.037 | 205 | 0/12 |

SS—Stainless steel
PE—Polyethylene
[a] k chosen to give 100 mg-sec/l area threshold
[c] $k_{5\ C.}$ calculated from $k_{30\ C.}$, vapor pressure data and decomposition rate factor
[d] k calculated as ($k_{3\ mm}$) × 3 surface to volume ratio × 3 diffusion radius ratio
[e] k calculated as ($k_{3\ mm}$) × 3.75 surface to volume ratio × 3.75 diffusion radius ratio
[f] k calculated as ($k_{1\ mm}$)/(3 surface to volume ratio × 3 diffusion radius ratio)

Shorter 3 mm×400 mm stainless steel lumens in Table 1 have the same rate constant as for 3 mm×500 mm lumens, because the materials and diameters are the same. However, the area is significantly greater for the shorter lumens, because the centers of these lumens are closer to the lumen entrances. When the injection times are reduced to two minutes and one minute from 6.5 minutes for 3 mm×400 mm stainless steel lumens, the areas drop to approximately 100 mg–sec/l, and positive biological indicators begin to appear. A positive biological indicator indicates that some test microorganisms have not been killed. If the temperature of these lumens is reduced from 30° C. to 5° C., the rate constant 0.46 sec$^{-1}$ must be corrected with kinetic and vapor pressure data to reflect the decreased decomposition rate and the increased condensation rate of hydrogen peroxide. The area with the corrected rate constant 1.41 sec$^{-1}$ falls below 100 mg–sec/l with a 6.5 minute injection time, and biological results are in the positive region.

Correcting the rate constant from 0.46 sec$^{-1}$ at 30° C. to 1.41 sec$^{-1}$ at 5° C. is initiated by writing the rate constant as the sum of the decomposition rate constant $k^D$ and the condensation rate constant $k^C$. At 30° C. the two rate constants can be assumed to be comparable in magnitude, because decomposition proceeds slowly near room temperature, while condensation is reduced in warm loads. For a rate constant 0.46 sec$^{-1}$ at 30° C., each individual rate constant of decomposition $k^D$ and condensation $k^C$ is approximately 0.46/2=0.23 sec$^{-1}$. The rate constant of condensation $k^C$ at 5° C. is calculated from the rate constant of condensation $k^C$ at 30° C. by adjusting it for the ratio of the vapor pressures of hydrogen peroxide at the two temperatures (*Hydrogen Peroxide*, Schumb et al., Reinhold Pub. Co., N.Y., 1955, p. 226): $k^C$ at 5° C.=0.23 sec$^{-1}$×(2.77 mm Hg at 30° C./0.46 mm Hg at 5° C.)=1.38 sec$^{-1}$. The rate constant of decomposition $k^D$ at 5° C. is calculated from the rate constant of decomposition $k^D$ at 30° C. and the rate factors for decomposition at 30° C. and 5° C.: $k^D$ at 5° C.=0.23 sec$^{-1}$×(1 rate factor at 5° C./7 rate factor at 30° C.)=0.03 sec$^{-1}$. The rate factors for decomposition of hydrogen peroxide are taken from Table 2 (Ref. FMC Technical Data Sheet, p. 10, rate increases 2.2 times per every 10° C.). Finally, the rate constant at 5° C. is calculated as the sum of the rate constants of condensation $k^C$ and of decomposition $k^D$ at 5° C.: k at 5° C.=1.38 sec$^{-1}$+0.03 sec$^{-1}$=1.41 sec$^{-1}$.

TABLE 2

Rate Factor for Decomposition of Hydrogen Peroxide as a Function of Temperature[a]

| Temperature, ° C. | Rate Factor for Decomposition |
|---|---|
| 5 | 1 Base Case |
| 15 | 2.2 |
| 25 | 4.84 |
| 35 | 10.65 |
| 45 | 23.4 |

[a]The decomposition rate increases by a factor of 2.2 for each 10° C. rise in temperature (Ref. FMC Technical Data Sheet, p. 10)

The solution equation is restricted to a one-dimensional model, so hydrogen peroxide transport in lumens would be treated similarly with 3 mm and with smaller diameters. However, experimental results demonstrate that efficacy in 1 mm and smaller diameter lumens can only be achieved in shorter lumen lengths. Therefore, the model needs to be adjusted to reflect the restricted transport in smaller lumens.

The adjustment for diameter is made in Table 1 by correcting the rate constant 0.46 $sec^{-1}$ for 3 mm stainless steel lumens to 4.14 $sec^{-1}$ for 1 mm lumens with factors for the surface to volume ratio and diffusion radius ratio. With this rate constant the area for 1 mm×125 mm lumens is greater than 100 mg–sec/l and the biological results are negative. The rate constant 0.46 $sec^{-1}$ is similarly corrected to 6.47 $sec^{-1}$ for 0.8 mm lumens; lumens with 100 mm length have area values greater than 100 mg–sec/l and negative biological results, while lumens at 150 mm length have areas lower than 100 mg–sec/l and positive biological results.

The correction of the rate constant 0.46 $sec^{-1}$ for surface to volume ratio is necessary, because 1 mm lumens have greater surface area inside the lumens for interaction with hydrogen peroxide molecules relative to the lumen volume, as compared to 3 mm lumens. The larger surface area contributes to a greater loss of hydrogen peroxide inside the smaller lumen, which is reflected in a greater rate constant.

Surface to volume ratio correction factor=(surface/volume)$_{1\ mm}$/(surface/volume)$_{3\ mm}$=($2\pi rL/\pi r^2 L$)$_{1\ mm}$/($2\pi rL/\pi r^2 L$)$_{3\ mm}$=($1/r$)$_{1\ mm}$/($1/r$)$_{3\ mm}$=($r$)$_{3\ mm}$/($r$)$_{1\ mm}$=1.5mm/0.5mm=3 where r represents the lumen or diffusion ratio.

In addition to correction for surface to volume ratio, correction of the rate constant 0.46 $sec^{-1}$ for diffusion radius is necessary, because diffusion to the wall of the smaller lumen is greater than for the larger one.

Diffusion radius ratio correction factor=($r$)$_{3\ mm}$/($r$)$_{1\ mm}$=1.5 mm/0.5 mm=3

The rate constant for the 1 mm lumen is calculated from the rate constant 0.46 $sec^{-1}$ for the 3 mm lumen and from the two factors for surface to volume ratio and diffusion radius ratio:

$k$ for 1 mm=0.46 $sec^{-1}$×3×3=4.14 $sec^{-1}$

A similar calculation is made for the rate constant for the 0.8 mm lumen:

$k$ for 0.8 mm=0.46 $sec^{-1}$×1.5/0.4×1.5/0.4=6.47 $sec^{-1}$

In this one-dimensional model for transport in the axial x direction in the lumen, radial transport effects are addressed by adjusting the rate constant. If the differential equation for the mass balance were stated in cylindrical coordinates instead of Cartesian coordinates, two-dimensional transport in the axial and radial directions would be represented in the solution, and no adjustment for lumen size would be required in the rate constant. However, the differential equation for transient two-dimensional transport with a reaction term has no analytical solution and must be solved numerically. The sterilizer computer 28 could be used to obtain an approximate solution to the two-dimensional model, but practical limits on the available on-board memory limit the preferred implementation of the model to the one-dimensional case.

The area scale for the second lumen material, polyethylene (PE), in Table 1 is established similarly for a limiting case in the STERRAD® 200 Sterilizer. The rate constant is set at 0.33 $sec^{-1}$ for 1 mm×500 mm lumens to give an area of approximately 100 mg–sec/l. Longer lumens 1 mm×700 mm with the same rate constant have an area less than 100 mg–sec/l with biological results in the positive region. The rate constant 0.33 $sec^{-1}$ for lumens with 1 mm diameter is corrected with factors for the surface to volume ratio and diffusion radius ratio to obtain the rate constant 0.037 $sec.^{-1}$ for 3 mm lumens. Area for 3 mm×1000 mm polyethylene lumens is greater than 100 mg–sec/l and the biological results are negative, while area for 3 mm×1500 mm lumens is about 100 mg–sec/l with positive biological results. By increasing the injection time in Table 1 from 6.5 minutes to 20, 25 and 30 minutes, the area for 3 mm×1500 mm lumens increases beyond the 100 mg–sec/l threshold and the biological results are negative.

If the results in Table 1 are rearranged according to the magnitude of area under the concentration-time curve, an interesting pattern becomes apparent in Table 3. All lumens with area greater than or equal to 110 mg–sec/l have only negative biological indicators. Lumens with area near 100 mg–sec/l have either negative or some positive indicators, while all lumens with area less than 90 mg–sec/l have at least one positive biological indicator. These results demonstrate that area under the concentration-time curve from the model correlates well with efficacy in a variety of lumen sizes and materials. Therefore, area may be used during the sterilization cycle as a tool in real time to accept or to cancel a sterilization cycle. The inputs to the model are readily available with sterilizer software. Process variables of pressure, concentration and time are monitored during the sterilization cycle, while the temperature, dimensions and composition of the most restrictive load element could be entered for each cycle by the operator. Devices 18 could be identified with a code, especially a machine readable code such as a bar code, which would either contain the physical parameters itself or relate to a set of parameters stored within the control system 26. The temperature of the lumen material, rather than being assumed as room temperature and entered, could be measured during the cycle.

TABLE 3

Results for the STERRAD ® 200 Sterilizer Arranged by Area under the Curve

| Lumen mm diam. × mm length | Temp. ° C. (lumen material) | Injection Time, min. | $-k$, $sec^{-1}$ | Mid-Lumen $H_2O_2$ Concentration vs. Time · Area, mg · sec./l | Fraction Positive BIs | Indicator Results Zone |
|---|---|---|---|---|---|---|
| 3 × 400 SS | 30 | 6.5 | 0.46 | 168, 156, 157 | 0/72 | Negative |
| 1 × 125 SS | 30 | 6.5 | 4.14 | 139, 143, 149 | 0/36 | |

TABLE 3-continued

Results for the STERRAD ® 200 Sterilizer Arranged by Area under the Curve

| Lumen mm diam. × mm length | Temp. °C. (lumen material) | Injection Time, min. | −k, sec$^{-1}$ | Mid-Lumen H$_2$O$_2$ Concentration vs. Time · Area, mg · sec./l | Fraction Positive BIs | Indicator Results Zone |
|---|---|---|---|---|---|---|
| 0.8 × 100 SS | 30 | 6.5 | 6.47 | 133, 137, 140, 136 | 0/48 | |
| 3 × 1000 PE | 30 | 6.5 | 0.037 | 262, 261, 245 | 0/36 | |
| 3 × 1500 PE | 30 | 20, 25, 30 | 0.037 | 179, 188, 205 | 0/36 | |
| 3 × 500 SS | 30 | 6.5 | 0.46 | 101, 93, 91 | 0/96 | Mixed |
| 3 × 400 SS | 30 | 2 | 0.46 | 106, 104, 108 | 0/72 | Positive and |
| 3 × 400 SS | 30 | 1 | 0.46 | 97, 100, 108 | 4/72 | Negative |
| 1 × 500 PE | 30 | 6.5 | 0.33 | 104, 107, 108 | 0/36 | |
| 3 × 1500 PE | 30 | 6.5 | 0.037 | 99, 102, 97 | 1/36 | |
| 3 × 400 SS | 5 | 6.5 | 1.41 | 53, 50, 50 | 1/72 | Positive |
| 0.8 × 150 SS | 30 | 6.5 | 6.47 | 43, 44 | 2/24 | |
| 1 × 700 PE | 30 | 6.5 | 0.33 | 34 | 1/12 | |

A special feature of this model is demonstrated in Table 3 for both polyethylene and stainless steel lumens. In the 3 mm×1500 mm polyethylene lumen an injection time of 6.5 minutes produces an area at the center of the lumen of about 100 mg–sec/l with biological results in the mixed zone. If this area were calculated during a sterilization cycle, the software could elect to increase the hydrogen peroxide exposure time (injection and/or diffusion step times) until the area increased to a value greater than or equal to 110 mg–sec/l to achieve efficacy. This approach is demonstrated in Table 3 in the cycles with 3 mm×1500 mm lumens for injection times of 20, 25 and 30 minutes. For these three cases, the areas are greater than or equal to 110 mg–sec/l and efficacy is achieved in all cases. A similar result is observed in 3 mm×400 mm stainless steel lumens. Injection times of 1 and 2 minutes correspond to areas near 100 mg–sec/l with biological indicators in the mixed zone, while increasing the injection time to 6.5 minutes produces areas greater than or equal to 110 mg–sec/l and only negative biological indicators. Employing area under the concentration-time curve in the sterilization cycle at a hydrogen peroxide transport-restricted region of the load, such as at the center 32 of the lumen 20, would improve sterilizer performance by reducing the number of canceled cycles. It would also offer an additional measurement for parametric release of the load to complement temperature, pressure and concentration in the chamber.

The studies in Table 1 were conducted at the minimum injection quantity of hydrogen peroxide necessary to achieve efficacy, but in practice the hydrogen peroxide solution injected into the sterilizer may be a greater quantity due to a larger injection volume or a greater initial solution concentration. In these cases, the area under the concentration-time curve would reach the threshold of 110 mg–sec/l at a shorter injection time, so the entire cycle time could be shortened to offer a benefit of quicker turn-around time for the operator.

If a load at a lower initial temperature were placed into the sterilizer, the pre-heating time of the cycle could be increased with plasma or convection heating to warm the load before injection to allow the area under the concentration-time curve to reach the threshold of 110 mg–sec/l. In this case, an initially cold load would not result in a cycle cancellation, so process performance would be enhanced by reducing the frequency of cycle cancellations.

Hydrogen peroxide exposure time, hydrogen peroxide injection quantity and load temperature before injection may all be used to increase the area under the concentration-time curve to the threshold of 110 mg–sec/l. As a result, process performance would be improved by reducing the frequency of cycle cancellation or by offering a shorter cycle time to the operator.

Although the foregoing description of the preferred embodiments of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. A method for assessing a sterilization of a lumen of a device in a vapor phase hydrogen peroxide sterilization process, the method comprising the steps of:
   a) measuring concentration of hydrogen peroxide vapor exterior of the lumen;
   b) calculating at least once a concentration of hydrogen peroxide at a selected location within the lumen based upon time of exposure, concentration of hydrogen peroxide exterior of the lumen and the physical characteristics of the lumen, wherein the calculation employs a mathematical model based upon a mass balance for hydrogen peroxide; and
   c) indicating a parameter relevant to said sterilization of said lumen based upon said concentration of said hydrogen peroxide at the selected location.

2. A method according to claim 1 wherein the step of indicating comprises displaying to a user said parameter relevant to the sterilization of the lumen.

3. A method according to claim 1 wherein the parameter relevant to the sterilization of the lumen comprises the concentration of said hydrogen peroxide at the selected location.

4. A method according to claim 1 wherein the method further comprises repeating steps a) and b) and calculating an integrated value of the concentration of hydrogen peroxide at the selected location over a time of exposure and wherein the parameter relevant to the sterilization of the lumen comprises said integrated value.

5. A method according to claim 1 wherein the parameter relevant to the sterilization of the lumen is success or failure of the sterilization of the lumen.

6. A method according to claim 1 wherein the process parameters used in the step of calculating at least once a concentration of hydrogen peroxide vapor at the selected location within the lumen comprise: pressure exterior of the lumen, the concentration of peroxide exterior of the lumen and time.

7. A method according to claim 1 wherein the physical characteristics of the lumen used in the step of calculating at least once a concentration of hydrogen peroxide vapor at the selected location within the lumen comprise: diameter of the lumen, length of the lumen to the selected location, type of material forming the lumen and temperature of the material forming the lumen.

8. A method according to claim 1 wherein step b) employs a mathematical model in which the lumen is assumed to have a single dimension.

9. A method according to claim 1 wherein step b) employs a mathematical model solved by iteration.

10. A method for controlling sterilization of a lumen of a device in a vapor phase hydrogen peroxide sterilization process, the method comprising the steps of:
   measuring a concentration of hydrogen peroxide vapor exterior of the lumen;
   calculating at least once a concentration of hydrogen peroxide at a selected location within the lumen based upon process parameters of the sterilization process and physical characteristics of the lumen, wherein the process parameters include the concentration of hydrogen peroxide exterior of the lumen, and wherein the calculation employs a mathematical model based upon a mass balance for hydrogen peroxide; and
   adjusting a parameter of the sterilization process based upon the at least one calculated concentration of hydrogen peroxide at the selected location.

11. A method according to claim 10 wherein the process parameters used in the step of calculating at least once a concentration of hydrogen peroxide vapor at the selected location within the lumen comprise: pressure exterior of the lumen, the concentration of peroxide exterior of the lumen and time.

12. A method according to claim 10 wherein the physical characteristics of the lumen used in the step of calculating at least once a concentration of hydrogen peroxide vapor at the selected location within the lumen comprise: diameter of the lumens length of the lumen to the selected location, type of material forming the lumen and temperature of the material forming the lumen.

13. A method according to claim 10 wherein the step of adjusting a parameter of the sterilization process comprises adjusting a time of exposure of the device to the vapor phase hydrogen peroxide.

14. A method according to claim 10 wherein the step of adjusting a parameter of the sterilization process comprises adjusting the concentration of the hydrogen peroxide exterior of the lumen.

15. A method according to claim 10 wherein the concentration of hydrogen peroxide exterior of the lumen is measured a plurality of times and a calculation of the concentration of hydrogen peroxide at the selected location is performed a plurality of times.

16. A method according to claim 15 and further comprising repeatedly measuring the concentration of hydrogen peroxide exterior of the lumen and calculating the concentration of hydrogen peroxide at the selected location and modifying a parameter of the sterilization process upon achieving a preselected value of hydrogen peroxide at the selected location.

17. A method according to claim 15 and further comprising the step of calculating an integrated time and concentration exposure of the selected location to the hydrogen peroxide.

18. A method according to claim 17 and further comprising the step of modifying a parameter of the sterilization process upon achieving a preselected value of the integrated time and concentration exposure at the selected location.

* * * * *